Figure 1:
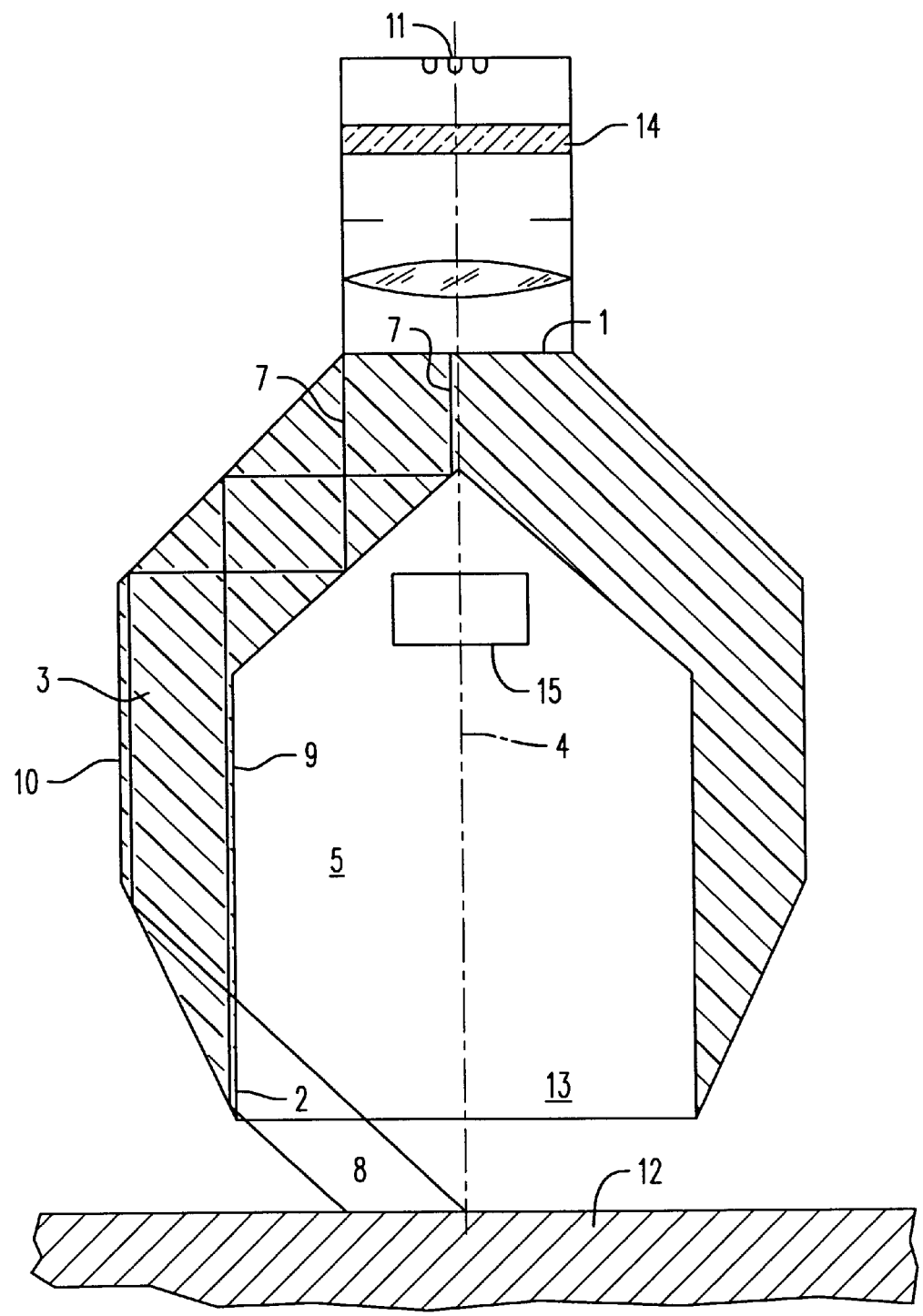

United States Patent
Schwarz

[11] Patent Number: 6,018,607
[45] Date of Patent: Jan. 25, 2000

[54] FIBER OPTIC LIGHT GUIDE FOR MEASUREMENT OF ILLUMINATION DEVICES

[75] Inventor: Peter Schwarz, Geretsried, Germany

[73] Assignee: BYK-Gardner, GmbH, Geretsried, Germany

[21] Appl. No.: 08/837,837

[22] Filed: Apr. 22, 1997

[30] Foreign Application Priority Data

Apr. 22, 1996 [DE] Germany .......................... 196 15 971

[51] Int. Cl.[7] .................................................. G02B 6/10
[52] U.S. Cl. ............................. 385/146; 385/12; 385/147
[58] Field of Search ............................... 385/146, 12, 13, 385/147, 125

[56] References Cited

U.S. PATENT DOCUMENTS

| | | | |
|---|---|---|---|
| 3,973,828 | 8/1976 | Onoda et al. .......................... | 385/125 |
| 4,039,845 | 8/1977 | Oberhansli et al. ...................... | 385/12 |
| 4,128,298 | 12/1978 | McMillan . | |
| 4,260,220 | 4/1981 | Whitehead ............................... | 385/125 |
| 4,688,883 | 8/1987 | Blaha ....................................... | 385/12 |
| 4,701,614 | 10/1987 | Jaeger et al. ............................ | 385/12 |
| 4,767,172 | 8/1988 | Nichols et al. ......................... | 385/146 |
| 5,144,689 | 9/1992 | Lovely .................................... | 385/12 |
| 5,309,544 | 5/1994 | Saxe . | |
| 5,363,464 | 11/1994 | Way et al. ............................... | 385/125 |
| 5,390,276 | 2/1995 | Tai et al. ................................. | 385/146 |
| 5,696,865 | 12/1997 | Beeson et al. .......................... | 385/146 |

FOREIGN PATENT DOCUMENTS

| | | |
|---|---|---|
| WO 94-25849 | 11/1994 | Germany . |
| 44 26 968 | 2/1996 | Germany . |
| 2-167838 | 6/1990 | Japan . |
| 07198952 | 8/1995 | Japan . |
| WO 94/25849 | 11/1994 | WIPO . |
| WO 96/27783 | 9/1996 | WIPO . |

*Primary Examiner*—Rodney Bovernick
*Assistant Examiner*—Ellen E. Kang
*Attorney, Agent, or Firm*—Ohlandt, Greeley, Ruggiero & Perle, L.L.P.

[57] ABSTRACT

A fiber optic light guide for a measurement or illumination system is described, in which an inside space left free in a fiber optic light guide unit is bounded laterally by a closed wall formed by the fiber optic light guide unit.

73 Claims, 2 Drawing Sheets

FIBER OPTIC LIGHT GUIDE FOR MEASUREMENT OF ILLUMINATION DEVICES

DESCRIPTION

The invention concerns a fiber optic light guide and a measurement system and illumination system constructed therewith and its method of manufacture.

The optical properties of surfaces and products, and particularly their colors, play a considerable role in the production industry and in branches of the service trade. As an example, we will name here the coloration of products of all types, such as, e.g., the painting of automobiles, etc., the printing industry, and here particularly the production of colored printed items, the production of cosmetic products, dental prostheses, the coloring and printing of textiles, etc. Colors also play an essential role in the reproduction of colored images in TV sets, computer monitors, as well as in color printers for computers.

In all products, in which the optical and particularly the color quality plays an essential role, these properties must be appropriately verified during and after production. This may be done manually, for example, by comparing the color print on the surface to be evaluated with a standardized color card. However, since such a comparison is very imprecise, in many cases it is indispensable to determine the optical properties and particularly the color properties by appropriate measurement devices and to quantitatively characterize them.

Usually, these measurement devices are constructed as reflection measurement devices, in which the sample is illuminated by an illumination device and the reflection is detected by a measurement sensor. Thus, in color measurements, it is preferred usually that either the illumination device emits light (or another suitable radiation) at an angle of 45° to the surface to be measured, whereas the measurement sensor is arranged perpendicularly to the measurement surface. Also, the reverse of this arrangement, in which the illumination is directed perpendicularly to the measurement surface and the measurement sensor is arranged at an angle of 45° to this surface for measurement of reflection, is frequently used.

A particular problem of today's measurement apparatus is the correct illumination of the measurement surface. Many surfaces do not reflect light homogeneously, i.e., the reflected light is dependent on the respective arrangement of the illumination device to the measurement sensor. Many textured surfaces, for example, the surface of textile fabrics, in which the surface is not smooth, but has a structured course dependent on the type of weave, etc. show such behavior. With such surfaces, the measurement result may depend on the orientation of the measurement device to the measurement surface in the azimuthal direction, so that with different azimuthal angles, different measurement results can be obtained.

In order to reduce the angular dependence of the measurement for such surfaces, it has been proposed to provide two or three illumination devices, which are displaced, for example, by 60° relative to one another and to arrange each at an angle of 45° to the measurement surface, whereby the measurement sensor is then aligned perpendicularly to the surface, i.e., in the direction of the surface normal line.

A fiber optic light guide for such a measurement or illumination device has been made known by PCT application WO94/25849. The publication shows a 45°/0° reflectance measurement structure, in which eight fiber-optic fiber bundles arranged at the same angular intervals are assigned to a central sensor, and these bundles receive light reflected by the sample at 45° and lead it to the sensor. Thus an eight-arm fiber-optic tentacle structure is connected to the sensor, whereby each tentacle arm corresponds to one fiber bundle.

The measurement devices known in the state of the art do not supply sufficiently good measurement results for specific surfaces, i.e., results that are independent of the alignment of the measurement apparatus. The known measurement devices are very elaborate in structure and they are particularly sensitive when fiber-optic tentacle arms are used, so that they are suitable particularly for laboratory operation, but not for continual quality control during production.

The invention takes on the task of providing a fiber optic light guide for a measurement or illumination system, a corresponding measurement or illumination system, and a corresponding manufacturing process, which overcome the named disadvantages of the state of the art and particularly permit a simple and cost-favorable, but simultaneously precise measurement.

This task is resolved by the invention with a fiber optic light guide according to Claim 1, a measurement system according to Claim 15, an illumination system according to Claim 19, a correspondingly combined measurement system according to Claim 27, and a manufacturing process according to Claim 28.

The fiber optic light guide unit according to the invention has an inside space, which is laterally surrounded by a closed wall formed by the fiber optic light guide unit. The term "lateral" is thus to be understood with respect to the longitudinal direction of the fiber optic light guide defined by the light input surface and the light output surface.

Even if the wall around the inside space and between the light input surface and the light output surface is as completely closed as possible, however, it may be necessary and advantageous to provide openings or guides in the wall for cables or for actuation or attachment elements for another device, particularly a measurement sensor arranged in the inside space. The term "closed" used in Claim 1 is to be understood in this sense.

The solution according to the invention has considerable advantages relative to arrangements known in the state of the art. In the fiber optic light guide according to the invention, the light is transmitted in such a way that it radiates onto the measurement surface simultaneously from all sides. In this way, a completely homogeneous illumination of the measurement surface is achieved, which completely excludes the influence of the illumination angle in the azimuthal direction.

On the basis of the very compact shape of the fiber optic light guide, the fiber optic light guide itself as well as an illumination device and measurement device constructed therewith can be designed in a very simple and structurally small manner, so that the measurement device, on the one hand, is inexpensive to manufacture and, on the other hand, is robust in operation.

As already mentioned, the inside space serves for the purpose of accommodating therein an additional device, perhaps an illumination or measurement device, depending on which device the fiber optic light guide itself belongs to. However, even devices that are very different from optical devices are conceivable, perhaps mechanical tools or manipulators, whereby the fiber optic light guide can serve for illumination and/or observation of the working field.

Further, the very simple geometry of a wall closed around an inside space, in comparison to the state of the art, offers further advantages with respect to measurements and technical manipulations. Since the entire azimuthal angle region is covered in a simple way with the fiber optic light guide according to the invention, textured materials, such as textiles, spooled materials such as yarn or double-twisted yarn, or other samples are reliably illuminated with azimuthal anisotropy. The utilization of the entire azimuthal angle region also has as a consequence a clear increase in light yield when compared to the state of the art, which is frequently decisive with respect to the light to be measured as well as with respect to illumination problems. In particular, the requirements for lamps or sensors to be used are reduced in this manner. Further, the closed geometry of the fiber optic light guide also offers an improvement in surface uniformity of the illumination or the measurement.

The simple geometry of the fiber optic light guide according to the invention, particularly its surface structure, also offers good possibilities for different surface coatings, which, as will be discussed below, can influence the reflection properties, and particularly can contribute to a diffuse mixing of the light.

With respect to manipulation, the compact, closed form is particularly favorable, thus perhaps with respect to application in limited spatial situations, in a production milieu, or for movable or portable systems. The insensitivity of the closed and compact structure according to the invention relative to mechanical stress and contamination produces practical advantages relative to handling. This robustness is excellent for practical application in optical apparatus employed in production.

Finally, the simple closed form can be produced essentially in a simpler way than the complex arrangement in the state of art, and in fact this applies to both the fiber optic light guide unit itself as well as the surface coating. It is also conceivable to form a fiber optic light guide unit configured according to the invention in a simple way with integrated optical components, as will be explained further below.

Particularly in connection with a suitable choice of materials for the fiber optic light guide unit, the simplified geometrical form can also make possible the applicability of particularly cost-favorable production processes, for example, injection molding, deep drawing, or machine blowing. Proceeding from a blank produced with such a mass-production process, the later properties of the fiber optic light guide can then be modified in a flexible manner by different surface treatments or coatings or even by changes in the initial materials utilized in the given shaping process.

The fiber optic light guide unit is a rigid unit in a simple and robust form of embodiment. It can conduct light in different ways, either by total reflection on the outer surface to the surrounding atmosphere or on a coated material with a lower index of refraction than that of the fiber optic light guide unit. However, a surface metallization may also be provided as a reflection layer. In particular, with respect to a controlled mixing of the light that is guided in the fiber optic light guide, a diffusely reflecting coating, particularly of barium sulfate is advantageous. Mixing properties, however, may also be effected by specific provision of fine inhomogeneities, thus inclusions, precipitations, streakings and the like, in the fiber optic light guide unit itself. This can be done by controlling the parameters in the production of the fiber optic light guide unit or also by an appropriate selection of the initial material. In any case, these measures lead to a very simple and cost-favorable way for a uniformly diffuse light mixing, when compared to the state of the art (e.g., Ulbricht's globe).

Particularly simple and advantageous forms of the fiber optic light guide of the invention have properties of symmetry, i.e., an axis of symmetry given in at least one cross-sectional plane relative to the longitudinal axis or a rotational symmetry around the longitudinal axis.

In many measurement applications, the values 45° and 0° (to the normal line of the specimen) have been utilized for the observation or illumination angles. Advantageously, the fiber optic light guide is thus shaped such that upon illumination with or detection of light beams that are parallel to the longitudinal axis at the light input or output surfaces, light beams are produced that lie essentially at an angle of 45° to the other light output or light input surfaces. In particular, in the inside space of the fiber optic light guide, a measuring/illuminating device can be provided under an angle of 0°. Further, a particularly simple and advantageous geometry results relative to the guiding of the light, if an inner wall of the fiber optic light guide unit runs parallel to an outer wall of the fiber optic light guide unit.

A preferred application of the fiber optic light guide of the invention is an optical measurement system, in which light emitted from a sample reaches one or more sensors, by passing through the light input surface, then the fiber optic light guide and finally through the light output surface and is measured. Therefore, for example, different sensors or sensors with different filters may be applied for a color measurement.

It is thus of advantage to accommodate an illumination device for the measurement system in the inside space of the fiber optic light guide. An opening arranged inside the light input surface between the inside space and the outside region can be provided in the fiber optic light guide. The illumination device can illuminate the sample through this opening. Further, it may be of advantage to configure the opening such that the illumination device can be built in or dismantled or maintained via this opening. Due to the danger of contamination or special cleaning requirements, however, it may also be meaningful to provide a transparent plate or an optical element for the illumination device instead of the opening, particularly to form a surface closed to the side of the sample. In a particular form of embodiment, the plate or the element may be designed in one piece with the fiber optic light guide. This front closed on the side of the sample that may be formed in one piece also contributes to the advantages of the invention that have already been mentioned above, relative to its compact construction.

Another possible application of the fiber optic light guide is in an illumination system, whereby, instead of the mentioned sensor, at least one lamp, perhaps an LED, is provided and the beam path is reversed, as it were, relative to the above-described application as a measurement system. This may be an illumination system for an optical measurement construction, or it may also be used for other purposes, for example, for general lighting purposes of a region that is to be accurately observed, particularly the operating field of a mechanical or other tool. As the lamp, an LED is advantageous, whereby, in particular, LEDs with an aperture angle of 6° or less may find application, which produce an extensively parallel beam bundle. If the lamp is adhered to the light input surface with a glue having an index of refraction corresponding to the fiber optic light guide unit, then this has advantages relative to simplicity of manufacture, compactness, and insensitivity of the illumination system, as well as, of course, optical advantages.

Within the scope of application for color measurement, it may be advantageous to provide several lamps for producing light of different colors.

Analogously to the utilization of the inside space of the above-described measurement system, a measurement device for detecting light reflected by a sample can also be accommodated in the inside space of the illumination system of the invention. The same is true for an opening in the light output surface of the illumination system or for a transparent plate or an optical element of the measurement device.

In particular, if measurements with 45°/0° geometry as well as those with 0°/45° geometry are desired, it may be advantageous to use a combined system, in which the fiber optic light guide of the invention is provided with at least one lamp and with at least one sensor, so that a selection can be made between operation as a measurement system or as an illumination system (each as described above). Correspondingly, a device that can be operated as a measurement and illumination device is provided in the inside space. The above designs are also valid accordingly.

The different possible applications of the fiber optic light guide are particularly advantageous relative to technical production. Therefore, essentially the same fiber optic light guide can be utilized once in order to guide light from an illumination device to the measurement surface and vice versa, to guide light reflected from the measurement surface to measurement sensors.

Finally, the invention also concerns a manufacturing method for fiber optic light guides, measurement or illumination systems according to the invention. As already mentioned, in particular, the fiber optic light guide can be manufactured by injection molding, deep drawing, or blowing, whereby it may be advantageous to mold it in at least two separate parts, which are then joined together. Here also, an adhesive with an index of refraction adapted to the fiber optic light guide unit may be applied.

Figure 2:
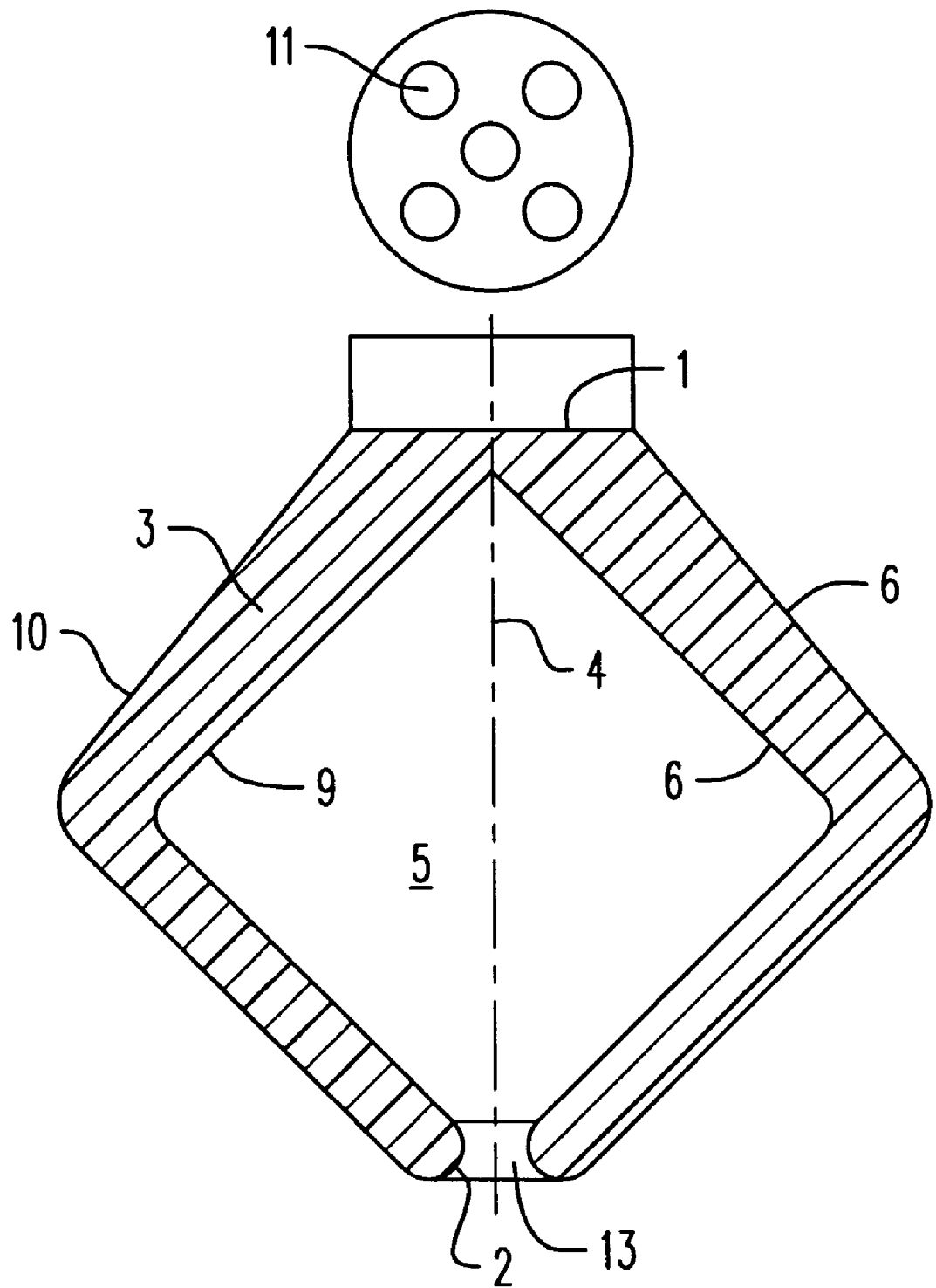

According to another preferred form of embodiment, the fiber optic light guide is configured in at least two parts in such a way that either the light input region with the light input surface and/or the light output region with the light output surface can be exchanged. In an essentially rotation-symmetric fiber optic light guide, this means that the fiber optic light guide is cut and separated in a plane perpendicular to this rotation-symmetric axis. The part that contains the light input surface and/or the light output surface is preferably configured so that it can be exchanged in this example of embodiment. This has the advantage that the characteristics of the light input surface and, which is particularly preferred, the characteristics of the light output surface may be modified by changing the part that includes this light input or light output surface. For illustration, the invention is described in the following on the basis of two examples of embodiment, which are shown in the figures. Here:

FIG. 1 shows a schematic cutaway view through an illumination device of the invention, and FIG. 2 shows a schematic cutaway view through another illumination device of the invention, whereby the upper part of the figure represents the arrangement of five LEDs on the light input surface.

FIG. 1 shows a fiber optic light guide, which is rotation-symmetric around the drawn-in longitudinal axis 4. The fiber optic light guide has a light input surface 1 at its upper end, and over this is arranged a separate optical device with several LEDs 11, a light-scattering disk 14 for diffuse homogenization of the light, a diaphragm, and a condenser lens for obtaining essentially parallel light beams 7 on light input surface 1.

Proceeding from light input surface 1, fiber optic light guide unit 3 is bounded by a cone-shaped inside surface 9 and a cone-shaped outer surface 10, which are inclined in section by 45° to longitudinal axis 4. A region is thus formed, in which the inside surface 9 and the outside surface 10 of the fiber optic light guide unit 3 are shaped as a cylinder. Then outer surface 10 bends inwardly at an angle of 22.5° in order to finally meet up with inside surface 9.

The distance of the cylindrically shaped region of inside surface 9 from longitudinal axis 4 corresponds approximately to the diameter of light input surface 1. The vertical distance between an upper pointed end of an inside space 5 enclosed by inside surface 9 relative to light input surface 1 and the wall thickness of fiber optic light guide unit 3 between the cylindrical region of inside surface 9 and outside surface 10 corresponds approximately to half of this distance. In this way, each beam from the parallel light beam bundle from the condenser reflects once at the cone-shaped region of inside surface 9 and once at the cone-shaped region of outside surface 10 and finally one more time at the lower oblique region of outside surface 10, so that it exits from fiber optic light guide unit 3 at an angle of 45° in the lower cylindrically shaped region of inside surface 9, i.e., a light output surface 2, and falls onto a sample arranged under the fiber optic light guide at an angle of 45° at 8.

There thus results a full illumination of the sample surface essentially at an angle of 45°, whereby, depending on the design of light-scattering disk 14, a more or less diffuse type of illumination can be selected. Depending on the distance between the fiber optic light guide and sample 12 each time, a round circular shaped or annular shaped illuminated field results on the sample.

The figure makes it clear that there is sufficient space in inside space 5 in order to provide a measurement or illumination device 15. In the case shown here, an opening 13 at the lower end of inside space 5 corresponds to the largest cross section of the inside space in the horizontal direction. Overall, fiber optic light guide unit 3 is designed in such a way that it can be injection molded in one piece from a transparent plastic. Walls 9 and 10 are metallized, with the exception of light output surface 2.

FIG. 2 shows a second example of embodiment, in which inside space 5 is bounded at the bottom by a clearly smaller opening 13. Fiber optic light guide unit 3 according to this example of embodiment is glued together from two individually injection-molded halves and is coated with barium sulfate on inside surface 9 and outside surface 10, with the exception of light input surface 1 and convex light output surface 2.

Because of the corresponding diffuse guidance of the light, the beam path is not defined individually; in particular, it depends less on the parallelness of inside surface 9 and outside surface 10. A circular disk-shaped mount with five individual LEDs is glued onto light input surface 1. Light input surface 1 can be dulled [frosted] in order to further reinforce the diffuse character of the illumination.

The above-described individual features can be essential for the invention in and of themselves or in any combination.

I claim:

1. A fiber optic light guide having a light input surface through which a light enters the fiber optic light guide, a light output surface through which the light exits the fiber optic light guide, and a transparent fiber optic light guide unit joining the light input surface and the light output surface and guiding the light entering the fiber optic light guide from the light input surface to the light output surface, the fiber optic light guide comprising:

a fiber optic light guide unit being formed in a closed manner laterally to a longitudinal direction defined by the light input surface and the light output surface around an inside space left free in the fiber optic light guide unit and from the light input surface up to the light output surface, a plurality of light beams essentially parallel to the longitudinal axis of the fiber optic light guide unit at the light input surface or the light output surface, said plurality of light beams correspond to a plurality of light beams lying essentially at an angle of 45° to the longitudinal axis on the light output surface or the light input surface, wherein said fiber optic light guide is a rigid unit, and wherein said inside space is laterally surrounded by a closed wall formed by said fiber optic light guide unit.

2. The fiber optic light guide according to claim 1, wherein the fiber optic light guide unit guides the light at least partially through total reflection.

3. The fiber optic light guide according to claim 1, further comprising a plurality of reflecting surfaces, wherein each one of said plurality of reflecting surfaces is coated at least partially with a material having a lower index of refraction than the fiber optic guide unit.

4. The fiber optic light guide according to claim 1, wherein the fiber optic light guide unit has a surface that is at least partially metallized and guides the light at least partially through reflection on the metallized surface.

5. The fiber optic light guide according to claim 1, wherein the fiber optic light guide unit is coated at least partially with a diffusely reflecting white material and guides the light at least partially through reflection on the material.

6. The fiber optic light guide according to claim 1, wherein the fiber optic light guide unit has fine inhomogenities distributed extensively statistically in it.

7. The fiber optic light guide according to claim 1, wherein the fiber optic light guide unit is axis-symmetrical relative to the longitudinal axis running through the light input surface and the light output surface.

8. The fiber optic light guide according to claim 7, wherein the fiber optic light guide unit is rotation-symmetrical relative to the longitudinal axis.

9. The fiber optic light guide according to claim 1, wherein the fiber optic light guide unit bounding the inside space has an inside wall that is at least partially parallel to an outside wall of the fiber optic light guide unit.

10. The fiber optic light guide according to claim 1, wherein one of the light input surface or the light output surface has a predetermined characteristic of light input or light output.

11. The fiber optic light guide according to claim 10, wherein the characteristic is selected from a group of characteristics consisting essentially of a parallel beam course, a divergent beam course, a convergent beam course, and a diffuse beam course.

12. The fiber optic light guide according to claim 10, wherein the fiber optic light guide unit has at least two parts, a first part that includes the light input surface or the light output surface, whereby the first part, can be exchanged in order to modify the characteristic of the light input and/or the light output.

13. A measurement system with a fiber optic light guide according to claim 1, wherein the fiber optic light guide takes up the light from a sample to be measured by the light input surface and leads the light to at least one sensor by means of the light output surface.

14. An illumination system with a fiber optic light guide according to claim 1, wherein the fiber optic light guide takes up light from at least one lamp by the light input surface and guides the light by the light output surface to a sample to be illuminated.

15. The process for the production of a fiber optic light guide according to claim 1, wherein the fiber optic light guide is injection-molded from a plastic material.

16. The process according to claim 15, wherein the fiber optic light guide is produced in at least two parts which are then joined together.

17. The process for the production of a fiber optic light guide according to claim 1, wherein the fiber optic light guide is blown from glass.

18. An illumination system with a fiber optic light guide, the fiber optic light guide having a light input surface through which a light enters the fiber optic light guide, a light output surface through which the light exits the fiber optic light guide, and a transparent fiber optic light guide unit joining the light input surface and the light output surface and guiding the light entering the fiber optic light guide from the light input surface to the light output surface, the fiber optic light guide comprising:

a fiber optic light guide unit being formed in a closed manner laterally to a longitudinal direction defined by the light input surface and the light output surface around an inside space left free in the fiber optic light guide unit and from the light input surface up to the light output surface;

wherein the fiber optic light guide takes up light from at least one lamp by the light input surface and guides the light by the light output surface to a sample to be illuminated; and a light scattering disk that is disposed between the at least one lamp and the light input surface or the light output surface and is formed as a light scattering surface.

19. The illumination system according to claim 18, wherein the fiber optic light guide unit is a rigid unit.

20. The illumination system according to claim 18, wherein the fiber optic light guide unit guides the light at least partially through total reflection.

21. The illumination system according to claim 18, further comprising a plurality of reflecting surfaces, wherein each one of said plurality of reflecting surfaces is coated at least partially with a material having a lower index of refraction than the fiber optic guide unit.

22. The illumination system according to claim 18, wherein the fiber optic light guide unit has a surface that is at least partially metallized and guides the light at least partially through reflection on the metallized surface.

23. The illumination system according to claim 18, wherein the fiber optic light guide unit is coated at least partially with a diffusely reflecting white material and guides the light at least partially through reflection on the material.

24. The illumination system according to claim 18, wherein the fiber optic light guide unit has fine inhomogenities distributed extensively statistically in it.

25. The illumination system according to claim 18, wherein the fiber optic light guide unit is axis-symmetrical relative to the longitudinal axis running through the light input surface and the light output surface.

26. The illumination system according to claim 25, wherein the fiber optic light guide unit is rotation-symmetrical relative to the longitudinal axis.

27. The illumination system according to claim 18, further comprising a plurality of light beams essentially parallel to the longitudinal axis of the fiber optic light guide unit at the light input surface or the light output surface that correspond to a plurality of light beams lying essentially at an angle of 45° to the longitudinal axis on the light output surface or the light input surface.

28. The illumination system according to claim 18, wherein the fiber optic light guide unit bounding the inside space has an inside wall that is at least partially parallel to an outside wall of the fiber optic light guide unit.

29. The illumination system according to claim 18, wherein one of the light input surface or the light output surface of the fiber optic light guide has a predetermined characteristic of light input or light output.

30. The illumination system according to claim 29, wherein the characteristic is selected from a group of characteristics consisting essentially of a parallel beam course, a divergent beam course, a convergent beam course, and a diffuse beam course.

31. The illumination system according to claim 29, wherein the fiber optic light guide unit has at least two parts, a first part that includes the light input surface or the light output surface, whereby the first part, can be exchanged in order to modify the characteristic of the light input and/or the light output.

32. The illumination system according to claim 18, wherein the at least one lamp is an LED having an aperture angle of 6° or less.

33. The illumination system according to claim 18, wherein the at least one lamp is adhered to the light input surface with an adhesive having an index of refraction corresponding to the fiber optic light guide unit.

34. The illumination system according to claim 18, wherein the at least one lamp is a plurality of lamps for generating light of different spectral characteristics.

35. The illumination system according to claim 18, further comprising a light scattering disk that is disposed between the at least one lamp and the light input surface or the light output surface and is formed as a light-scattering surface.

36. The illumination system according to claim 18, wherein the inside space has an opening arranged inside the light output surface and a measurement device measures the light through the opening.

37. The illumination system according to claim 18, further comprising a transparent plate or an optical element of the measurement device is arranged inside the light output surface, whereby the light output surface and the plate or the element form a closed surface to the side of the sample.

38. An illumination system with a fiber optic light guide, the fiber optic light guide having a light input surface through which a light enters the fiber optic light guide, a light output surface through which the light exits the fiber optic light guide, and a transparent fiber optic light guide unit joining the light input surface and the light output surface and guiding the light entering the fiber optic light guide from the light input surface to the light output surface, the fiber optic light guide comprising:
- a fiber optic light guide unit being formed in a closed manner laterally to a longitudinal direction defined by the light input surface and the light output surface around an inside space left free in the fiber optic light guide unit and from the light input surface up to the light output surface,
- wherein the fiber optic light guide takes up light from at least one lamp by the light input surface and guides the light by the light output surface to a sample to be illuminated,
- wherein the light is transmitted by the fiber optic light guide unit such that it radiates onto the sample simultaneously from all sides excluding an influence of an illumination angle in the azimuthal direction, and
- a measurement device arranged in the inside space for measurement of the light reflected from the sample.

39. The illumination system according to claim 38, wherein the fiber optic light guide unit is a rigid unit.

40. The illumination system according to claim 38, wherein the fiber optic light guide unit guides the light at least partially through total reflection.

41. The illumination system according to claim 38, further comprising a plurality of reflecting surfaces, wherein each one of said plurality of reflecting surfaces is coated at least partially with a material having a lower index of refraction than the fiber optic guide unit.

42. The illumination system according to claim 38, wherein the fiber optic light guide unit has a surface that is at least partially metallized and guides the light at least partially through reflection on the metallized surface.

43. The illumination system according to claim 38, wherein the fiber optic light guide unit is coated at least partially with a diffusely reflecting white material and guides the light at least partially through reflection on the material.

44. The illumination system according to claim 38, wherein the fiber optic light guide unit has fine inhomogenities distributed extensively statistically in it.

45. The illumination system according to claim 38, wherein the fiber optic light guide unit is axis-symmetrical relative to the longitudinal axis running through the light input surface and the light output surface.

46. The illumination system according to claim 45, wherein the fiber optic light guide unit is rotation-symmetrical relative to the longitudinal axis.

47. The illumination system according to claim 38, further comprising a plurality of light beams essentially parallel to the longitudinal axis of the fiber optic light guide unit at the light input surface or the light output surface that correspond to a plurality of light beams lying essentially at an angle of 45° to the longitudinal axis on the light output surface or the light input surface.

48. The illumination system according to claim 38, wherein the fiber optic light guide unit bounding the inside space has an inside wall that is at least partially parallel to an outside wall of the fiber optic light guide unit.

49. The illumination system according to claim 38, wherein one of the light input surface or the light output surface of the fiber optic light guide has a predetermined characteristic of light input or light output.

50. The illumination system according to claim 49, wherein the characteristic is selected from a group of characteristics consisting essentially of a parallel beam course, a divergent beam course, a convergent beam course, and a diffuse beam course.

51. The illumination system according to claim 49, wherein the fiber optic light guide unit has at least two parts, at least a first part that includes the light input surface or the light output surface, whereby the first part can be exchanged in order to modify the characteristic of the light input and/or the light output.

52. The illumination system according to claim 38, wherein the at least one lamp is an LED having an aperture angle of 6° or less.

53. The illumination system according to claim 38, wherein the at least one lamp is adhered to the light input surface with an adhesive having an index of refraction corresponding to the fiber optic light guide unit.

54. The illumination system according to claim 38, wherein the at least one lamp is a plurality of lamps for generating light of different spectral characteristics.

55. The illumination system according to claim 38, further comprising a light scattering disk that is disposed between the at least one lamp and the light input surface or the light output surface and is formed as a light-scattering surface.

56. The illumination system according to claim 38, wherein the inside space has an opening arranged inside the light output surface and the measurement device measures the light through the opening.

57. The illumination system according to claim 38, further comprising a transparent plate or an optical element of the measurement device is arranged inside the light output surface, whereby the light output surface and the plate or the element form a closed surface to the side of the sample.

58. A measurement system with a fiber optic light guide, having a light input surface through which a light enters the fiber optic light guide, a light output surface through which the light exits the fiber optic light guide, and a transparent fiber optic light guide unit joining the light input surface and the light output suface and guiding the light entering the light output light guide from the light input surface to the light output surface, the fiber optic light guide comprising:

a fiber optic light guide unit being formed in a closed manner laterally to a longitudinal direction defined by the light input surface and the light output surface around an inside space left free in the fiber optic light guide unit and from the light input surface up to the light output surface, wherein the fiber optic light guide takes up the light from a sample to be measured by the light input surface and leads the light to at least one sensor by means of the light output surface, wherein said fiber optic light guide unit is a rigid unit, wherein said inside space is laterally surrounded by a closed wall formed by said fiber optic light guide unit, and an illumination device arranged in the inside space for illumination of the sample.

59. The measurement system according to claim 58, wherein the fiber optic light guide unit guides the light at least partially through total reflection.

60. The measurement system according to claim 58, further comprising a plurality of reflecting surfaces, wherein each one of said plurality of reflecting surfaces is coated at least partially with a material having a lower index of refraction than the fiber optic guide unit.

61. The measurement system according to claim 58, wherein the fiber optic light guide unit has a surface that is at least partially metallized and guides the light at least partially through reflection on the surface metallization.

62. The measurement system according to claim 58, wherein the fiber optic light guide unit is coated at least partially with a diffusely reflecting white material and guides the light at least partially through reflection on the material.

63. The measurement system according to claim 58, wherein the fiber optic light guide unit has fine inhomogenities distributed extensively statistically in it.

64. The measurement system according to claim 58, wherein the fiber optic light guide unit is axis-symmetrical relative to the longitudinal axis running through the light input surface and the light output surface.

65. The measurement system according to claim 58, wherein the fiber optic light guide unit is rotation-symmetrical relative to the longitudinal axis.

66. The measurement system according to claim 58, further comprising a plurality of light beams essentially parallel to the longitudinal axis of the fiber optic light guide unit at the light input surface or the light output surface that correspond to a plurality of light beams lying essentially at an angle of 45° to the longitudinal axis on the light output surface or the light input surface.

67. The measurement system according to claim 58, wherein the fiber optic light guide unit bounding the inside space has an inside wall that is at least partially parallel to an outside wall of the fiber optic light guide unit.

68. The measurement system according to claim 58, wherein one of the light input surface or the light output surface of the fiber optic light guide has a predetermined characteristic of light input or light output.

69. The measurement system according to claim 68, wherein the characteristic is selected from a group of characteristics consisting essentially of a parallel beam course, a divergent beam course, a convergent beam course, and a diffuse beam course.

70. The measurement system according to claim 68, wherein the fiber optic light guide unit has at least two parts, at least a first part that includes the light input surface or the light output surface, whereby the first part can be exchanged in order to modify the characteristic of the light input and/or the light output.

71. The measurement system according to claim 58, wherein the fiber optic light guide unit has an opening arranged within the light input surface and the illumination device illuminates the sample through the opening.

72. The measurement system according to claim 58, further comprising a transparent plate or an optical element of the illumination device arranged inside the light input surface, whereby the light input surface and the plate or the element form a closed surface to the side of the sample.

73. A measurement system according to claim 58, wherein the device arranged in the inside space can be operated as a measurement or an illumination device, and the fiber optic light guide unit leads the light correspondingly from at least one lamp to the sample or leads the light reflected by the sample to at least one sensor, whereby the at least one lamp and the sensor are adjacent to one another on the side of the fiber optic light guide turned away from the sample.

* * * * *

UNITED STATES PATENT AND TRADEMARK OFFICE
CERTIFICATE OF CORRECTION

PATENT NO. : 6,018,607

DATED : January 25, 2000

INVENTOR(S) : Peter Schwartz

It is certified that error appears in the above-identified patent and that said Letters Patent is hereby corrected as shown below:

Claim 58, column 11, line 16, delete "light output" and insert --fiber optic--.

Signed and Sealed this

First Day of May, 2001

Attest:

NICHOLAS P. GODICI

Attesting Officer    Acting Director of the United States Patent and Trademark Office